United States Patent [19]

Bither, Jr.

[11] 4,442,226

[45] Apr. 10, 1984

[54] CATALYST FOR VAPOR PHASE OXIDATION OF N-BUTANE TO MALEIC ANHYDRIDE

[75] Inventor: Tom A. Bither, Jr., Wilmington, Del.

[73] Assignee: E. I. Du Pont de Nemours and Company, Wilmington, Del.

[21] Appl. No.: 421,467

[22] Filed: Sep. 22, 1982

Related U.S. Application Data

[62] Division of Ser. No. 349,305, Feb. 16, 1982, Pat. No. 4,371,702.

[51] Int. Cl.$^3$ .............................................. B01J 27/14
[52] U.S. Cl. .................................... 502/209; 502/214
[58] Field of Search ................................ 252/435, 437

[56] References Cited

U.S. PATENT DOCUMENTS

| | | | |
|---|---|---|---|
| B 330,354 | 1/1975 | Mount et al. ........................ | 352/437 |
| 3,864,280 | 2/1975 | Schneider ........................... | 252/435 |
| 4,062,802 | 12/1977 | Bertolacini et al. ................ | 252/435 |
| 4,062,873 | 12/1977 | Harrison .......................... | 260/346.75 |
| 4,064,070 | 12/1977 | Harrison ............................ | 252/435 |
| 4,111,963 | 9/1978 | Mount et al. ..................... | 260/346.75 |
| 4,132,670 | 1/1979 | Katsumoto et al. ................ | 252/437 |
| 4,151,116 | 4/1979 | McDermott ........................ | 252/435 |
| 4,187,235 | 2/1980 | Katsumoto et al. .............. | 260/346.75 |
| 4,225,465 | 9/1980 | Bremer ............................... | 252/435 |
| 4,244,878 | 1/1981 | McDermott .................... | 260/346.75 |
| 4,283,288 | 8/1981 | Udovich et al. .................... | 252/437 |
| 4,283,307 | 8/1981 | Barone et al. ...................... | 252/432 |

*Primary Examiner*—William G. Wright

[57] ABSTRACT

Improved vanadium/phosphorus oxide catalyst for the vapor phase oxidation of n-butane to maleic anhydride, and the use of said catalyst to prepare maleic anhydride, said catalyst containing the nonpost-deposited promoter comprising silicon and at least one of indium, antimony and tantalum.

12 Claims, No Drawings

CATALYST FOR VAPOR PHASE OXIDATION OF N-BUTANE TO MALEIC ANHYDRIDE

CROSS-REFERENCE TO RELATED APPLICATIONS

This is a division of application Ser. No. 349,305 filed Feb. 16, 1982, and issued Feb. 1, 1983 as U.S. Pat. No. 4,371,702.

DESCRIPTION

1. Technical Field

This invention relates to an improved vapor phase oxidation process for the preparation of maleic anhydride from n-butane based upon use of a catalyst containing mixed oxides of vanadium and phosphorus modified by a promoter.

2. Background

The preparation of mixed oxide compositions of vanadium and phosphorus and the use of these as catalysts for the oxidation of hydrocarbons to maleic anhydride is known in the art. In U.S. Pat. No. B330,354 and U.S. Pat. No. 4,111,963 the importance of reducing the vanadium used in a vanadium/phosphorus/oxygen catalyst to the +4 oxidation state is described. Preferred is the use of concentrated hydrochloric acid as the reaction medium to bring about this reduction and preferred catalysts have a phosphorus to vanadium atom ratio of 1:2 to 2:1 and a porosity of at least 35%. In U.S. Pat. No. 3,864,280 the reduction of the vanadium in such a catalyst system to an average valence state of 3.9 to 4.6 is emphasized; the atomic ratio of phosphorus to vanadium is 0.9–1.8:1. Isobutyl alcohol is used as a solvent for the catalyst preparation, with the indication that an increase in catalyst surface area, over that obtained from use of an aqueous system, is achieved. The addition of promoters to the vanadium/phosphorus oxide catalyst compositions used for the oxidation of hydrocarbons to maleic anhydride is also disclosed in the art. Thus, in U.S. Pat. No. 4,062,873 and U.S. Pat. No. 4,064,070 are disclosed vanadium/phosphorus/silicon catalyst compositions made in an organic medium. In U.S. Pat. No. 4,132,670 and U.S. Pat. No. 4,187,235 are disclosed processes for preparing high surface area vanadium/phosphorus oxide catalysts. Anhydrous alcohols of 1–10 carbon atoms and 1–3 hydroxyl groups are used to reduce the vanadium to a valence of 4.0 to 4.6. Also disclosed are such catalysts containing up to 0.2 mol, per mol of vanadium, of a transition, alkali or alkaline earth metal, for example, tantalum, titanium, niobium, antimony, bismuth or chromium. U.S. Pat. No. 4,151,116 and U.S. Pat. No. 4,244,878 disclose vanadium/phosphorus catalysts having an element selected from magnesium, calcium, scandium, yttrium, lanthanum, cerium, uranium, chromium, manganese, iron, cobalt, nickel, copper, zinc, aluminum, gallium, indium, silicon, germanium, tin, antimony, bismuth and tellurium post-deposited on the surface. Optionally, the catalyst includes an integrally-incorporated promoting or activating element selected from titanium, zinc, hafnium, lithium, magnesium, calcium, iron, cobalt, nickel, copper, tin, bismuth, uranium, the rare earth metals, chromium, cadmium, and aluminum.

In any commercial process for the production of maleic anhydride from n-butane it is important that the yield of maleic anhydride be as high as possible, that is, the product of n-butane conversion and selectivity to maleic anhydride should be maximized. Thus, in a process in which the off-gases following recovery of maleic anhydride are combusted, a high single-pass yield is of import. In a recycle-type of operation wherein unconverted n-butane is returned to the oxidizer following removal of maleic anhydride, a high single-pass yield is also desirable in order to avoid reprocessing excessive amounts of hydrocarbon.

Albeit the fact that the art discloses the use of promoters in the improved vanadium/phosphorus oxide catalyst systems used in the oxidation of hydrocarbons to maleic anhydride, there remains a need for improved processes for maleic anhydride production. Such is an object of this invention. Another object is to provide an improved vanadium/phosphorus oxide catalyst system. Still other objects will become apparent hereinafter.

DISCLOSURE OF INVENTION

For further comprehension of the invention, and of the objects and advantages thereof, reference may be made to the following description and to the appended claims in which the various novel features of the invention are more particularly set forth.

The invention herein resides in an improved process for preparing maleic anhydride by the catalytic oxidation of n-butane, and in an improved catalyst for carrying out such a process. More specifically, the catalyst employed in the process is a vanadium/phosphorus oxide catalyst containing the promoter comprising silicon and at least one of the variable valent elements selected from indium, antimony and tantalum. Still more specifically, the invention herein resides in:

1. the improved catalytic process for the oxidation of n-butane to maleic anhydride using a vanadium/phosphorus oxide catalyst, the improvement consisting of using a vanadium/phosphorus oxide catalyst containing the promoter comprising silicon and at least one of indium, antimony and tantalum, said catalyst being prepared by the procedure wherein the appropriate vanadium species is first contacted with the promoter or promoter precursors and thereafter with the appropriate phosphorus species; and 2. the improved vanadium/phosphorus oxide catalyst for the oxidation of n-butane to maleic anhydride, said improved catalyst containing the promoter comprising silicon and at least one of indium, antimony and tantalum and being prepared by the procedure wherein the appropriate vanadium species is contacted with the promoter or promoter precursors and thereafter with the appropriate phosphorus species so that the catalyst contains the promoter in nonpost-deposited form, that is, integrally associated throughout the catalyst rather than merely on the surface thereof.

It is to be understood that the above recitations of the invention do not include those process steps which are well known and commonly used in the preparation of vanadium/phosphorus oxide catalysts. Following are additional details on the preparation of the catalyst of the invention.

The improved vanadium/phosphorus oxide catalyst of this invention to bring about the vapor phase oxidation of n-butane to maleic anhydride is made by a process wherein a conventional vanadium compound wherein the vanadium is in the +5 oxidation state, such as in $V_2O_5$ or $NH_4VO_3$, is initially reduced to a substantial degree to the +4 oxidation state by reaction in either an aqueous or organic liquid medium. In an aqueous medium, the reductant can comprise a soluble inorganic compound, such as a halide acid, for example, concentrated hydrochloric acid; a reduced acid of phosphorus, for example, H₃PO₃; or a soluble organic compound, for example, formaldehyde, ethylene glycol, or glycolic, oxalic, citric or tartaric acid. In an organic medium, the preferred medium herein, the reductant can comprise an alcohol(s) selected from such species as n-propyl, isopropyl, n-butyl, isobutyl, and benzyl alcohols. The reduction can be brought about by slurrying the pentavalent vanadium compound in the liquid medium, followed by heating under reflux for the necessary time to bring about reduction.

The improvement in the vanadium/phosphorus oxide catalyst system of this invention, which leads to enhanced productivity of maleic anhydride, results from the introduction of a promoter which is a combination of selected materials, preferably introduced in both a specific order and chemical form, following the reduction step in which the tetravalent vanadium species is formed. As indicated, the promoter comprises silicon and at least one of the variable valent elements selected from indium, antimony and tantalum. In the improved catalyst of the invention the Si/V atom ratio is in the range 0.02–3.0:1.0, and the (In+Sb+Ta)/V atom ratio is in the range 0.005–0.2:1.0, preferably 0.02–0.12:1.0. The P/V atom ratio is in the range 0.9–1.3:1.0. A significant feature of the invention, namely, the introduction of the promoter comprising at least two specific elements, during or after the reduction of the vanadium to the tetravalent species, before the vanadium is contacted with the phosphorus species, readily distinguishes the invention from similar catalysts wherein one or more promoters are post-deposited on the vanadium/phosphorus oxide.

In the aqueous system for preparing the catalyst of the invention the silicon can be introduced in the form of a colloidal silica sol, for example, as one of the Ludox ® colloidal silica compositions commercially available from E. I. du Pont de Nemours and Company. In the organic system, for example, an alcoholic system, the silicon can be added as an alkyl orthosilicate, for example, tetraethyl orthosilicate. When using an orthosilicate and V₂O₅ it is preferable to add at least 0.25 mol of orthosilicate per mol of V₂O₅ following substantial reduction of the +5 vanadium to the +4 vanadium species.

Although not necessary to the basic performance of the modified vanadium/phosphorus oxide catalyst of this invention, it is preferred that the indium, antimony and/or tantalum be introduced into the reaction medium as soluble species. Thus, in the organic system, they can be added as a cation with an appropriate attendant anion, for example, an acetate, alkoxide, or anhydrous halide. Although the addition of the indium, antimony and/or tantalum compound can be carried out during the reduction of the pentavalent vanadium species, it is preferred that this addition take place subsequent to the initial charge of silicon compound, for example, an alkyl orthosilicate, in order to preclude and/or minimize hydrolysis thereof to a less desirable oxide species of indium, antimony and/or tantalum prior to the ultimate addition of the requisite phosphorus compound which completes the formation of the catalyst precursor. The hydrolytic formation of and/or the primary addition of indium, antimony and/or tantalum as slurried oxides, although still giving operable catalysts, leads to more polyphase products showing macro segregation of the adducts in the final catalyst, particularly at higher levels of addition.

Following substantial reduction of the +5 vanadium to the tetravalent species and the introduction of the requisite promoter or promoter precursors the catalyst precursor is formed by the addition of any commonly used appropriate phosphorus compound, for example, phosphoric acid, in such amount that the P/V atom ratio in the ultimate catalyst is in the range 0.9–13:1.0, with continued heating of the resultant mixture under reflex to give the catalyst precursor composition that can be isolated by filtration, following cooling of the slurry to room temperature. This product is subsequently dried in air at 80°–200° C. It is a crystalline species having an x-ray diffraction pattern (Cu Kα) with the following major peaks:

| d-value, Å | Intensity, I/I₀ |
|---|---|
| 5.70 | 100 |
| 4.52 | 43 |
| 3.67 | 29 |
| 3.29 | 37 |
| 3.11 | 17 |
| 2.94 | 54 |
| 2.79 | 14 |
| 2.66 | 16 |
| 1.90 | 11 |

This catalyst precursor is then formed into a convenient catalyst shape, for ultimate charge into a reactor, by gently crushing through a 20-mesh sieve (U.S. Sieve Series), blending the resultant powder with 1–3% of a die lubricant and pellet binder, such as graphite or Sterotex ®, a hydrogenated cottonseed oil, commercially available from Capital City Products Co., and tableting to either ⅛" or 3/16" (3.2 or 4.8 mm) diameter pellets.

The pelleted catalyst precursor is fired in a controlled manner in order both to generate and activate the catalyst species for use in the vapor phase oxidation of n-butane to maleic anhydride. Typically, unactivated pellets charged into a 1" (2.54 cm) diameter quartz tube in a vertical furnace are heated, first, in a low flow of air (about 1–3 volumes/volume of catalyst/minute) at 375°–400° C. for 1–6 hours, and then, in a more rapid gas flow (about 3–6 volumes/volume of catalyst/minute) of 1–1.5% n-butane in air (by volume) at 450°–490° C. for about 16–24 hours. The resultant pellets are then ready for use in the production of maleic anhydride. In general, conventional conditions are employed for the n-butane oxidation.

The vapor phase oxidation of n-butane to maleic anhydride can be carried out using, in general, conventional techniques, for example, in a fixed-bed reactor by contacting the activated catalyst species with n-butane and oxygen, in appropriate concentrations, in the presence of one or more inert diluent gases. Air provides a satisfactory source of oxygen. Synthetic mixtures of oxygen and such diluent gases as nitrogen, argon, helium and water vapor may also be used. The explosive potential of a wide range of oxygen-butane mixtures combined with inert diluent gases must be recognized. Thus, a concentration of up to about 1.5–2.0% (by volume) butane in air represents the maximum safe range for the lower explosive limit. At an oxygen concentration reduced to about 10%, the restriction on butane no longer pertains. The modified vanadium/phosphorus oxide catalysts described herein show a sensitivity to oxygen partial pressure with respect to their catalytic activity. As a consequence, it is preferred that the oxygen level in the feed be maximized within the limits of safe operability. In order to achieve maximum productivity of maleic anhydride, it is also desirable to maximize the butane concentration under the same regimen.

It is preferred to carry out the oxidation of n-butane to maleic anhydride at a hydrocarbon concentration of about 1.5% in air (by volume) for a fixed-bed type of operation. The oxidation is carried out in the temperature range 300°–550° C., preferably, at 350°–450° C. Operating pressures can vary from about 0.5 to 20 atmospheres (50 to 2000 kPa), but are preferably in the range 1 to 7 atmospheres (100 to 700 kPa), and more preferably, in the range of 2 to 4 atmospheres (200 to 400 kPa). Contact times, as expressed at standard temperature and pressure, can vary from about 0.1 to 15.0 seconds, preferably, from about 0.2–4.0 seconds.

The oxidation of n-butane to maleic anhydride with the catalyst of this invention can also be carried out in a fluidized-bed reactor. Due to the nature of the performance of a fluidized bed reactor, oxidation of n-butane to maleic anhydride can be conducted at concentrations heretofore referred to as falling within the explosive region. Catalysts for use in this type of system can comprise particles in the approximate size range 60–325 mesh (U.S. Sieve Series). These can be generated by crushing and sieving pre-formed catalyst pellets whose preparation has been described previously. The desired particle size distribution for this type of catalyst may also be achieved by spray drying slurries of the catalyst precursor at appropriate concentrations. To enhance attrition resistance, variable amounts of a support, such as silica, can be incorporated into the fluid-bed catalyst system by the addition of a colloidal silica sol, for example, as one of the Ludox ® colloidal silica compositions commercially available from E. I. du Pont de Nemours and Company, or a very finely-divided silica powder, such as one of the Cab-O-Sil ® fumed silicas commercially available from the Cabot Corporation.

Of the following thirty-six examples, twelve are outside the invention and are presented for comparison with the remaining examples. The examples outside the invention are designated in the tables by asterisks. The amounts of In, Ta and Sb used in the examples are given in atom %, that is, the atom ratio of In/V multiplied by 100, the atom ratio of Ta/V multiplied by 100, and the atom ratio of Sb/V multiplied by 100; the amount of Si present is given as weight % of the total weight of the catalyst.

EXAMPLE 1

This example demonstrates the formation of a catalyst containing silicon and indium as promoter, and the use thereof in the preparation of maleic anhydride.

A 1-L, 3-neck flask equipped with stirrer, reflux condenser, and heating mantle was charged with 50 g of $V_2O_5$, 500 ml of isobutyl alcohol, and 50 ml of benzyl alcohol. To this was added 3.16 g of In metal (corresponding to 5 atom % In) which had been dissolved initially in hydrochloric acid, then taken to dryness on a steam bath, followed by redissolving in a minimum volume of glacial acetic acid (dried down twice from acetic acid prior to preparing final solution containing indium as indium acetate). This mixture was heated at reflux for one hour to bring about reduction of the $V_2O_5$. $Si(OEt)_4$ (15 g) was then introduced through a dropping funnel, and the mixture was heated at reflux for two more hours. At this time, an additional 45 g of $Si(OEt)_4$ was added, followed by 73 g of 85% $H_3PO_4$. The initial dark-green mixture was heated at reflux overnight to give a light-blue slurry. Following cooling, this solid was filtered off and air dried, first at 120° and then at 200° C. The resultant gray-green solid (103 g) showed the standard catalyst precursor x-ray pattern and differential scanning calorimetry indicated a large endotherm at about 450° C. during up-heat under an atmosphere of $N_2$.

This solid was blended with 2% of Sterotex ® and pelleted for firing. Twenty-four g (30 cc) of these pellets were charged into a 1" (2.54 cm) diameter quartz tube mounted vertically in an electrically-heated furnace and were initially fired in a down-flowing (45 cc/min) stream of air while heating 2 hours to 375° C., followed by 2¼ hours at about 375° C. The die lubricant and residual solvents in the pellets were removed at this stage. n-Butane at about 1.5% (by volume) concentration was introduced into the air stream, and the total flow rate was increased to about 135 cc/min. The temperature was raised to about 478° C. in one-half hour and was held for about 16 hours. The temperature was then dropped to about 250° C. to avoid an uncontrolled exotherm in the catalyst bed, and the flow of 1.5% butane in air was increased to 500 cc/min. The temperature was slowly raised to 420° C., and oxidation of butane to maleic anhydride was carried out under these conditions for 7 hours. Following cooling under an atmosphere of $N_2$, 20 g of sturdy, uniformly light-brown catalyst pellets was obtained. Their surface area was 30 m$^2$/g, the average vanadium valence was about +4.0, and analysis showed a silica content of 1.33 wt. %. All valence determinations herein were carried out using conventional chemical titrations.

EXAMPLE 2

This example demonstrates the formation of a catalyst containing silicon, antimony and tantalum and the use thereof in the preparation of maleic anhydride.

A 1-L, 3-neck flask equipped with stirrer, reflux condenser, and heating mantle was charged with 50 g of $V_2O_5$, 500 ml of isobutyl alcohol, and 50 ml of benzyl alcohol. This mixture was heated at reflux for one hour; 16 g of $Si(OEt)_4$ was introduced through a dropping funnel and reflux was continued for two more hours. Ten g of tantalum ethoxide, $Ta(OEt)_5$, corresponding to 4.5 atom % Ta, and 8.4 g of antimony butoxide, $Sb(O-Bu)_3$, corresponding to 4.5 atom % Sb, each dissolved in 25 ml of absolute ethanol, were then added to the reaction mixture. Following a one-hour heat under reflux, 45 g of $Si(OEt)_4$ was added and after an additional heating period of one hour, 81 g of 85% $H_3PO_4$ was added. The reactants were heated at reflux overnight and, following cooling, a light-blue solid was isolated by filtration and dried, first on a steam bath and then in a vacuum oven. This product (98 g) showed the usual catalyst precursor x-ray pattern.

It was blended with 2% Sterotex ® and pelleted 3/16" (4.8 mm) and the "green" (unactivated) pellets were subsequently crushed gently to a "through 10- on 20-mesh" (U.S. Sieve Series) particle size for firing.

Fifty-nine g (55 cc) of the 10–20 mesh granules were heated in flowing air (83 cc/min) in a 1" (2.54 cm) diameter quartz tube in a vertical furnace to about 380° C. in 2 hours and were then maintained at about 381°–397° C. for 2½ hours. A stream of 1.5% n-butane in air (by volume; 200 cc/min) was then passed over these particles while raising the temperature to 480°–485° C. in 1½ hours. This was maintained overnight. After dropping the catalyst bed temperature to 250° C., 500 cc/min of 1.5% butane in air (by volume) was flowed over this catayst for about 5 hours at a temperature of 425–430° C. to produce maleic anhydride. Following cooling, 49 g of sturdy, uniformly gray catalyst particles was obtained. Their surface area was 28 m²/g, and the average vanadium valence was about +4.0.

EXAMPLES 3–36

Data from Examples 3–36 are presented in Tables I, II and III to demonstrate the relative performance of various vanadium/phosphorus oxide catalysts, prepared, in general, by the procedures described in Examples 1 and 2. The catalysts were tested under different sets of operating conditions used to prepare maleic anhydride from n-butane. The catalysts comprised vanadium/phosphorus oxides wherein: (a) no promoter was present; (b) Si, alone, was present; (c) the elements In or Ta, alone, were present; and (d) the combination Si plus at least one of In, Ta and Sb was present; (a), (b) and (c) are outside the invention. In addition, comparisons were made between adding In, Ta and Sb as insoluble oxides and adding in a form soluble in the reaction medium.

The source of Si for Examples 3–36 was Si(OEt)$_4$. For those examples in which In, Ta and/or Sb were added in insoluble form, the oxides were used. When In, Ta and/or Sb were added in soluble form, acetates, alkoxides, and halides were used. The catalyst and its reactivity are substantially independent of the choice of the soluble compound used.

EXAMPLES 3–16

Vertical Fixed-Bed Quartz Reactor of 1″ (2.54 cm) Diameter

The data presented in Table I were obtained in the following manner. Pelleted catalyst precursor, either of 3/16″ (4.8 mm) diameter as formed or subsequently crushed to "through 10- on 20-mesh" (U.S. Sieve Series) particle size, weighing in the range of about 50–100 g, was charged into a 1″ (2.54 cm) diameter quartz tube in a 3-zone, electrically-heated vertical furnace and pre-conditioned: (1) in air at about 380° C., and (2) in 1.5% butane in air (by volume) at about 480° C., as described in Example 2. A clean receiver was then put in place to collect maleic anhydride, a gas flow of 1.5% n-butane in air (by volume), calculated to give a contact time at standard temperature and pressure of about 2–4 seconds, was passed over the catalyst, and the hotspot temperature was adjusted to about 420° C. After a reaction time of about 6–30 hours (usually about 24 hours), at a pressure of about one atmosphere (100 kPa), the reactor was cooled under flowing N$_2$, the maleic anhydride collected was dissolved in water, and the total amount produced was determined by titration of duplicate aliquots. The mol, single-pass yield of maleic anhydride, as reported in Table I, was calculated as the quotient of the number of mols of maleic anhydride produced during a given time divided by the number of mols of n-butane delivered in the feed gas during the same time interval, times 100.

The data shown in Table I demonstrate the performance of unmodified and silica(only)-modified V/P/O$_x$ catalyst compositions (Examples 3 and 4, outside the invention). As pointed out in the patent art, these compositions represent good catalysts for the preparation of maleic anhydride from n-butane. Examples 5 and 6 (also outside the invention) show the performance of Ta (added as the insoluble Ta$_2$O$_5$) and In (added as the soluble acetate) in the absence of the requisite Si. These catalysts are definitely inferior to those of the invention. Example 7 shows the performance of In (added as the nsoluble oxide) and Si. Although such catalyst is within the invention, it is not as good as catalysts of the invention prepared from soluble additives, as shown in Examples 8–16.

EXAMPLES 17–20

Titanium U-Tube Fixed-Bed Reactor of ¼″ (6.4 mm) Diameter

The data presented in Table II were obtained in the following manner. Pre-activated catalyst in the range 20–40 mesh (U.S. Sieve Series) particle size and weighing about 4–5 g was charged into a titanium U-tube reactor of ¼″ (6.4 mm) diameter. This reactor, which was heated in a fluidized sand-bath to achieve good temperature control, was connected so as to allow on-line transport of both feed and product streams at a temperature somewhat over 200° C. (both as a feed pre-heat and to avoid deposition of maleic anhydride) from a feed manifold through the reactcr and then on to dual gas chromatographic (GC) facilities. Insertion of a heated back-pressure valve in the exit line ahead of the GC train allowed operation of this system from atmospheric pressure (100 kPa) to a maximum of about 125 psia (about 860 kPa), at a catalyst contact time of about 1.8 seconds at standard temperature and pressure. The analytical train allowed determination of N$_2$, O$_2$, CO, CO$_2$, H$_2$O, n-butane, maleic anhydride, and compounds such as ethylene, furan, and methyl ethyl ketone, with the latter three appearing only in trace amounts when the oxidation reaction of this invention proceeded in a normal manner. With the catalysts described herein, CO was formed in larger amounts than CO$_2$, with the CO/CO$_2$ ratio usually in the range of 2.0–1.3:1.0.

Catalyst productivity, that is, a measure of the effectiveness of a given quantity of catalyst to provide a desired product, should be high. This property, also known as Space Time Yield (STY) is defined herein as the number of grams of maleic anhydride (MA) produced per kilogram of catalyst charged per hour of operating time. High yields of maleic anhydride, coupled with high gas flows over the catalyst will maximize this productivity. Very high gas flows at an operating pressure of but one atmosphere (100 kPa) will not necessarily generate good productivity, however, since the contact time of the feed stream over the catalyst bed may be of too short duration. By increasing reaction pressure, the contact time can be increased for a given gas flow, and if the mass and heat transfer properties of the catalyst are adequate, the yield of product will not be appreciably diminished due to adverse side reactions.

The data listed in Table II include the productivity of two catalysts of the art; Example 17 shows an unmodified V/P/O$_x$ catalyst and Example 18 shows such a catalyst modified with Si. Example 18 has been divided into two parts, Example 18A employing the same feed composition of Example 17, Example 18B employing a feed composition which is similar to those employed in Examples 19 and 20. It is to be noted that the productivities of catalysts of Example 19 (made from a soluble Ta compound) and Example 20 (made from a soluble In compound), both catalysts of the invention, are higher than those of their unmodified counterparts of the art at pressures above about 75 psia (about 520 kPa). The catalysts of the art appear to lose activity (that is, conversion) with increasing reaction pressure, whereas the catalysts of Examples 19 and 20 show a modest enhancement in this property.

EXAMPLES 21-36

Titanium Fixed-Bed Reactor of ¼" (6.4 mm) Diameter With a Diluted Bed

In a highly exothermic reaction such as the catalyzed vapor phase oxidation of n-butane to maleic anhydride, the maintenance of isothermal operating conditions can lead to increased productivity, due to elimination of severe hot spotting in the catalyst bed. Operation in this mode becomes a favorable means of evaluating the relative performance of a series of catalysts under elevated pressure. Toward this end, the data presented in Table III were obtained in the following manner. Catalyst particles in the size range 40-60 mesh (U.S. Sieve Series), weighing 1.5 g, were blended with 2.4 g of acid-washed silicon carbide of the same particle size distribution and were charged into a titanium reactor of ¼" (6.4 mm) diameter. With this configuration of diluted catalyst particles and small reactor diameter, isothermal reaction conditions prevail. Six reactors, loaded in this manner, were heated, in two sets of three, in two fluidized sandbaths to achieve good temperature control. These reactors were connected into an automated system that allowed controlled on-line transport of feed over the catalysts and automatic analyses of the resultant product streams. Reactions were carried out through a predetermined, program-controlled temperature sequence from 340° to 525° to 340° C. in a series of 11 steps, with a 2-hour hold at each temperature to allow both equilibration of the reaction and analysis of the products from each reactor. Reactions were carried out at pressures of 25 or 115 psia (about 170 or about 795 kPa) at a constant mass flow of 350 cc/min, with a feed consisting of 1.8% n-butane/10.0% $O_2$/88.2% $N_2$. From the resultant butane conversion and maleic anhydride selectivity vs. temperature curves readily constructed from the data, the peak yield of maleic anhydride was determined for each catalyst. Such yield data are shown in Table III.

Examples 21-23 (outside the invention) of Table III show productivity data for unmodified and silica-modified V/P/$O_x$ compositions. They represent good catalysts for the preparation of maleic anhydride from n-butane, as defined in the patent art. Examples 24-26 (also outside the invention) show the performance of Ta (added both in soluble and insoluble form) as a modifier in the absence of silica. As seen here, and from the data in Table I, these catalysts are not as effective as the catalysts of the invention. Examples 27-36 demonstrate the overall enhanced performance of the catalyst of this invention. Although Example 30, which involved the use of an insoluble additive, is somewhat better than the controls, it is to be noted that addition of the same atom percent of Ta in soluble form (Example 31) leads to improved catalyst performance.

TABLE I

Vapor Phase Oxidation of n-Butane to Maleic Anhydride in a 1" (2.54 cm) Diameter Vertical Fixed-Bed Quartz Reactor

| Ex. No. | V/P/O Catalyst Promoter Atom % In | Ta | Sb | Wt. % SiO$_2$ | In, Ta, Sb Added in Soluble or Insoluble Form | % Maleic Anhydride Single-Pass Yield |
|---|---|---|---|---|---|---|
| 3* | 0 | 0 | 0 | 0 | — | 53 |
| 4* | 0 | 0 | 0 | 2 | — | 50 |
| 5* | 0 | 5 | 0 | 0 | Insol | 27 |
| 6* | 2 | 0 | 0 | 0 | Sol | 31, 41 |
| 7 | 2 | 0 | 0 | 2 | Insol | 53 |
| 8 | 3 | 0 | 0 | 2 | Sol | 55, 63 |
| 9 | 5 | 0 | 0 | 2 | Sol | 65 |
| 10 | 0 | 2 | 0 | 2 | Sol | 54 |
| 11 | 2 | 3 | 0 | 2 | Sol | 59 |
| 12 | 3 | 9 | 0 | 2 | Sol | 55 |
| 13 | 3 | 0 | 7 | 2 | Sol | 72 |
| 14 | 5 | 0 | 5 | 2 | Sol | 70 |
| 15 | 0 | 3 | 2 | 2 | Sol | 57 |
| 16 | 1 | 3 | 1 | 2 | Sol | 55 |

TABLE II

Vapor Phase Oxidation of n-Butane to Maleic Anhydride in a ¼" (6.4 mm) Diameter Titanium U-Tube Fixed-Bed Reactor

| Ex. No. | V/P/O Catalyst Promoter Atom % In | Ta | Wt. % SiO$_2$ | Feed Mol % n-butane | O$_2$ | N$_2$ | Reaction Conditions Temp °C. | Press (psia) | Press (kPa) | Total Rx Time at P (Hrs) | Results n-butane % Conv. | MA % Select | STY |
|---|---|---|---|---|---|---|---|---|---|---|---|---|---|
| 17* | 0 | 0 | 0 | 1 | 5 | 94 | 420 | 16 | 110.3 | 5 | 51 | 67 | 18 |
|  |  |  |  |  |  |  |  | 55 | 379.2 | 22 | 32 | 72 | 40 |
|  |  |  |  |  |  |  |  | 95 | 654.9 | 3 | 19 | 75 | 43 |
|  |  |  |  |  |  |  |  | 115 | 792.8 | 3 | 18 | 74 | 48 |
| 18a* | 0 | 0 | 2 | 1 | 5 | 94 | 420 | 16 | 110.3 | 4 | 43 | 73 | 16 |
|  |  |  |  |  |  |  |  | 75 | 517.1 | 22 | 29 | 76 | 50 |
|  |  |  |  |  |  |  |  | 115 | 792.8 | 4 | 28 | 75 | 74 |
| 18b* | 0 | 0 | 2 | 2.3 | 10.0 | 87.7 | 420 | 16 | 110.3 | 5 | 34 | 72 | 29 |
|  |  |  |  |  |  |  |  | 75 | 517.1 | 19 | 30 | 69 | 107 |
|  |  |  |  |  |  |  |  | 95 | 654.9 | 4 | 26 | 62 | 105 |
| 19 | 0 | 10 | 2 | 2.7 | 10.0 | 87.3 | 400 | 15 | 103.4 | 19 | 38 | 66 | 24 |
|  |  |  |  |  |  |  |  | 60 | 413.6 | 20 | 44 | 65 | 101 |
|  |  |  |  |  |  |  |  | 75 | 517.1 | 25 | 49 | 63 | 132 |
|  |  |  |  |  |  |  |  | 90 | 620.5 | 5 | 48 | 60 | 149 |
| 20 | 5 | 0 | 1.3 | 2.5 | 10.0 | 87.5 | 400 | 15 | 103.4 | 2 | 20 | 76 | 16 |
|  |  |  |  |  |  |  |  | 65 | 448.1 | 19 | 32 | 70 | 98 |
|  |  |  |  |  |  |  |  | 90 | 620.5 | 3 | 31 | 70 | 142 |

TABLE III

Isothermal Vapor Phase Oxidation of n-Butane to Maleic Anhydride in a ¼" (6.4 mm) Diameter Titanium Reactor With Diluted Fixed-Bed

| Ex. No. | V/P/O Catalyst Promoter Atom % In | Ta | Sb | Wt. % SiO$_2$ | In, Ta, Sb Added in Soluble or Insoluble Form | STY ca 170 kPa | STY ca 795 kPa |
|---|---|---|---|---|---|---|---|
| 21* | 0 | 0 | 0 | 0 | — | 284 | 162 |
| 22* | 0 | 0 | 0 | 2 | — | 233 | — |
| 23* | 0 | 0 | 0 | 2 | — | 214 | 273 |
| 24* | 0 | 10 | 0 | 0 | Insol | 131 | — |
| 25* | 0 | 5 | 0 | 0 | Insol | 214 | 273 |
| 26* | 0 | 10 | 0 | 0 | Sol | 146 | 131 |
| 27 | 0 | 10 | 0 | 2 | Sol | — | 467 |
| 28 | 0 | 5 | 0 | 2 | Sol | — | 414 |
| 29 | 0 | 2½ | 0 | 2 | Sol | — | 388 |
| 30 | 0 | 5 | 0 | 2 | Insol | 295 | 295 |
| 31 | 0 | 5 | 0 | 2 | Sol | 340 | 364 |
| 32 | 5 | 0 | 0 | 2 | Sol | 329 | 273 |
| 33 | 3 | 0 | 0 | 2 | Sol | — | 362 |
| 34 | 5 | 0 | 5 | 2 | Sol | 306 | 440 |
| 35 | 3 | 0 | 7 | 2 | Sol | 317 | 253 |
| 36 | 3 | 9 | 0 | 2 | Sol | 317 | 273 |

EXAMPLE 37

Fluid Bed Reactor of ½" (12.7 mm) Diameter

A portion of the pre-activated catalyst used in Examples 14 and 34 was crushed and sieved to obtain the following particle size distribution (U.S. Sieve Series): 100–140 mesh (35%), 140–200 mesh (50%), 200–325 mesh (15%). A 7 g sample of this mixture (surface area of 24 m$^2$/g, average vanadium valence +4.03, SiO$_2$ content 2.1 wt. %) was charged into a fluid-bed type reactor consisting of a catalyst chamber of ½" (12.7 mm) diameter titanium tubing about 3½ (8.9 cm) high, followed by a 3" (7.6 cm) long expansion chamber about 1" (2.54 cm) in diameter. The entering feed stream was preheated by passage over 10–12 mesh (U.S. Sieve Series) SiC and was dispersed into the catalyst chamber through a plug of glass wool. This reactor was heated in a fluidized sandbath and connected into the feed system and on-line analysis facilities as described in Examples 17–20. The feed stream supplied to this reactor analyzed about 1.7% n-butane/10.0% O$_2$/88.3% N$_2$. After 41 hours on stream in a fluidized mode (395° C., 15 psia, about 100 kPa, contact time of 2.8 seconds) a 78% conversion, at 65% selectivity, of n-butane to maleic anhydride was obtained. In a second run of 46 hours at 437° C., 15 psia, about 100 kPa, contact time of 2.8 seconds, an 84% conversion, at 60% selectivity, of n-butane to maleic anhydride was obtained.

BEST MODE FOR CARRYING OUT THE INVENTION

The best modes demonstrating the improved process of preparing maleic anhydride from n-butane and the improved catalyst for use in the process are demonstrated in Examples 1, 2, 7 to 16, 19, 20 and 27 to 36.

INDUSTRIAL APPLICABILITY

Maleic anhydride is a well known chemical intermediate which is useful in the production of alkyd resins. It also can be converted to butanediol which is useful in the production of polyester resins.

Although the above disclosure illustrates and describes preferred embodiments of the invention, it is to be understood that there is no intent to limit the invention to the precise constructions herein disclosed, and it is to be further understood that the right is reserved to all changes and modifications coming within the scope of the invention as defined in the appended claims.

I claim:

1. Improved vanadium/phosphorus oxide catalyst for the oxidation of n-butane to maleic anhydride, said improved catalyst containing the promoter comprising silicon and at least one of indium, antimony and tantalum, the Si/V atom ratio being in the range 0.02–3.0:1.0, the (In+Sb+Ta)/V atom ratio being in the range 0.005–0.2:1.0 and the P/V atom ratio being in the range 0.9–1.3:1.0, said catalyst being prepared in an aqueous or organic liquid medium by the procedure wherein the appropriate vanadium species substantially of valence +4 is contacted with the promoter or promoter precursors and thereafter with the appropriate phosphorus species.

2. Catalyst of claim 1 wherein the (In+Sb+Ta)/V atom ratio is in the range 0.02–0.12:1.0.

3. Catalyst of claim 1, the catalyst being prepared in an organic liquid medium.

4. Catalyst of claim 3 wherein, in the catalyst preparation, the appropriate vanadium species substantially of valence +4 is first contacted with an appropriate silicon compound and thereafter with an appropriate compound or compounds of at least one of indium, antimony and tantalum.

5. Catalyst of claim 4 wherein, in the catalyst preparation, the appropriate compound of silicon and compound or compounds of at least one of indium, antimony and tantalum are soluble in the organic liquid medium.

6. Improved vanadium/phosphorus oxide catalyst for the oxidation of n-butane to maleic anhydride, said improved catalyst containing the nonpost-deposited promoter comprising silicon and at least one of indium, antimony and tantalum, the Si/V atom ratio being in the range 0.02–3.0:1.0, the (In+SB+Ta)/V atom ratio being in the range 0.005–0.2:1.0, and the P/V atom ratio being in the range 0.9–1.3:1.0.

7. Catalyst of claim 6 wherein the (In+Sb+Ta)/V atom ratio is in the range 0.02–0.12:1.0.

8. Catalyst of claim 6, the catalyst being prepared in an aqueous or organic liquid medium.

9. Catalyst of claim 8, the catalyst being prepared in an organic liquid medium.

10. Catalyst of claim 9, the catalyst being prepared by the process comprising contacting the appropriate vanadium species substantially of valence +4 with the promoter or promoter precursors and thereafter with the appropriate phosphorus species.

11. Catalyst of claim 10 wherein, in the catalyst preparation, the appropriate vanadium species substantially of valence +4 is first contacted with an appropriate silicon compound and thereafter with an appropriate compound or compounds of at least one of indium, antimony and tantalum.

12. Catalyst of claim 11 wherein, in the catalyst preparation, the appropriate compound of silicon and compound or compounds of at least one of indium, antimony and tantalum are soluble in the organic liquid medium.

* * * * *